United States Patent [19]

Kuronō et al.

[11] Patent Number: 4,734,411

[45] Date of Patent: Mar. 29, 1988

[54] PYRROLIZIDINE COMPOUNDS, SALTS THEREOF, PROCESS FOR THE PREPARATION OF SAME AND PHARMACEUTICAL AGENTS COMPRISING SAME

[75] Inventors: Masayasu Kuronō, Mie; Yasuaki Kondo, Kasugai; Takuji Yamaguchi, Kuwana; Toshinao Usui, Gifu; Ryoichi Unno, Nagoya; Hiromoto Kimura, Kasugai; Masato Fukushima, Komaki; Mitsuru Oka, Kusugai; Shinichi Ikeda, Kusugai; Noboru Kuboyama, Kusugai; Takashi Ito, Kasugai; Seiji Miyano, Fukuoka; Kunihiro Sumoto, Ohnojo, all of Japan

[73] Assignee: Sanwa Kagaku Kenkyusho Co., Ltd., Aichi, Japan

[21] Appl. No.: 895,099

[22] Filed: Aug. 11, 1986

[30] Foreign Application Priority Data

Sep. 4, 1985 [JP] Japan .................................. 60-193834

[51] Int. Cl.⁴ ....................... A61K 31/55; C61K 31/54; C07D 521/00; C07D 519/00
[52] U.S. Cl. ................................: 514/220; 514/223; 514/224; 540/495; 544/43
[58] Field of Search .......................... 540/495; 544/43; 514/220, 223, 224

[56] References Cited

U.S. PATENT DOCUMENTS 3,987,042  10/1976  Gueremy et al. ..................... 544/43

Primary Examiner—Robert T. Bond
Attorney, Agent, or Firm—Armstrong, Nikaido, Marmelstein & Kubovcik

[57] ABSTRACT

Novel pyrrolizidine compounds represented by the formula

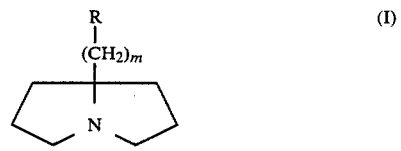

wherein
R is a radical of

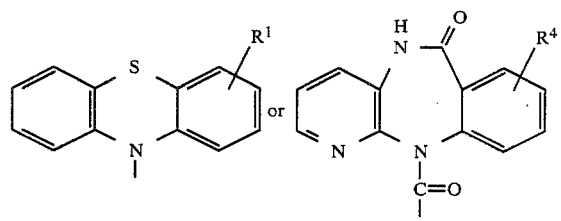

$R^1$ is hydrogen, halogen, alkyl group, alkoxy group, alkanoyl group, trifluoromethyl radical, trimethylsilyl radical or

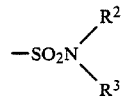

$R^2$ and $R^3$ are same or different and are hydrogen or alkyl group, respectively, $R^4$ is hydrogen, halogen, alkyl group or alkoxy group and m is an integer of 0 to 5, salts thereof, a process for the preparation of same as well as a pharmaceutical agent comprising same.

9 Claims, No Drawings

PYRROLIZIDINE COMPOUNDS, SALTS THEREOF, PROCESS FOR THE PREPARATION OF SAME AND PHARMACEUTICAL AGENTS COMPRISING SAME

BACKGROUND OF THE INVENTION

1. Field of the Invention

The present invention relates to novel pyrrolizidine compounds, salts thereof, a process for the preparation of same as well as pharmaceutical agents comprising same. Each of the compounds and salts shows an antiulcer activity and more particularly, against gastric ulcer.

2. Related Arts

Pharmaceutical agents for curing gastric ulcer can generally be classified into those suppressing offensive factors and those strengthening defensive factors. Among them, the former has greatly been developed but on the latter, it is fact that a development thereof makes slow progress and a study thereon now reaches to find a clue for dissolving the matter.

It has been a well known fact that the gastric juice as the offensive factor plays an important role on the gastric ulcer, in view of developmental pathology thereon and thus a suppression of its digestion power has been made as a main target for curing the gastric ulcer. Therefore, hitherto, the suppression of digestive power of the gastric juice, according to an antacid and inhibition of gastric secretion by mainly an agent having anticholine action have been employed as main curing measures. However, the former has a disadvantage in that an effective acting period of time is short and while the latter has also a disadvantage in that the agent may cause side effects of corediastasis, an exaggeration of glaucoma, tachycardia and the like depending on suppression of muscarinic receptor.

In recent years, antagonistic agents to a receptor of parietal cell have appeared as a new type anti-ulcer. Such agents have been watched with a great interest, since those are characterized by having a prolonging action on inhibition of gastric secreti in the stomach and show an actionof promoting a cure of ulcer, which is unique in comparison with and can not be found in the anti-ulcer agents which had been known at that time.

As exemplar antagonistic agents to the receptor of parietal cell Cimetidine of that to histaminic II receptor and Pirenzepine of a selective antagonistic agent to muscarinic receptor may be listed. It has been said those have little side effects in degree but the cimetidine have side effects of forming a perforation in ulcer and strengthening a delayed hypersensitive reaction and the pirenzepine shows side reactions due to supression of muscarinic receptor, although those are somewhat weak.

SUMMARY OF THE INVENTION

A primary object of the invention is to provide novel compounds and salts for curing gastric ulcer, each of which has a strong pharmacological activity but show no or quite weak side effect to give an excellent agent in both of effectiveness and safety in use.

A secondary object of the invention is to provide a process for preparing such compounds as well as pharmaceutical agents for curing gastric ulcer, which comprises at least one of the compounds and salts, as an effective component therefor.

According to the invention, the primary object can be attained by a novel pyrrolizidine compound represented by the formula

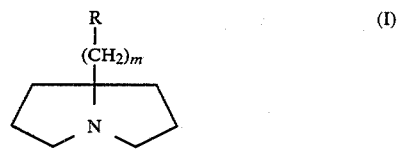

wherein
R is a radical of

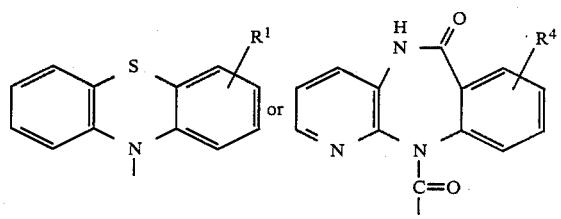

$R^1$ is hydrogen, halogen, alkyl group, alkoxy group, alkanoyl group, trifluoromethyl radical, trimethylsilyl radical or

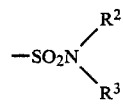

$R^2$ and $R^3$ are same or different and are hydrogen or alkyl group, respectively, $R^4$ is hydrogen, halogen, alkyl group or alkoxy group and m is an integer of 0 to 5,
or a salt of the compound.

Namely, it has been confirmed that each of the compounds shown by Formula (I) and salts thereof has a strong anti-ulcer activity and show a quite weak side effect.

In the compound of Formula (I), the term of "halogen" may be fluorine, chlorine, bromine or iodine. The "alkyl group" may be straight-chain alkyl radicals, branched-chain alkyl radicals or cycloalkyl radicals. As examples for the straight-chain alkyl radicals, one having 1 to 6 carbon atoms, for instance methyl, ethyl, n-propyl, n-butyl, n-pentyl, n-hexyl and the like may be listed. As examples for the branched-chain alkyl radicals, isopropyl, isobutyl, s-butyl, t-butyl and the like may be listed. As examples for the cycloalkyl radicals, cyclopropyl, cyclobutyl, cyclopentyl, cyclohexyl and the like may be listed. As examples for the alkoxy group, methoxy, ethoxy, n-propoxy, isopropoxy, n-butoxy, isobutoxy, s-butoxy, t-butoxy and the like may be listed. As examples for the alkanoyl group, acetyl, propionyl and the like may be listed.

In the specification, the salt of the compounds (I) means pharmacologically acceptable one. As examples for acids to form the salt, hydrogen chloride, sulfuric acid and hydrogen bromide or the like mineral acid as well as fumaric acid, maleic acid or the like organic acid may be listed.

According to the invention, among the compounds shown by Formula (I), those represented by the formula

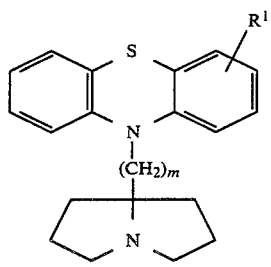

(I-a)

wherein $R^1$ and m have the meanings as referred to, can be prepared by subjecting to react in the presence of a base a compound represented by the formula

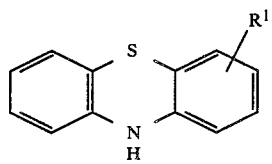

(II)

wherein $R^1$ has the meaning as referred to, with a compound represented by the formula

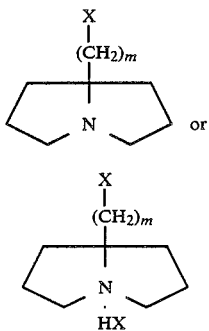

(III-a)

or (III-b)

wherein m has the meaning as referred to and X is halogen.

As the base, alkali carbonates such as sodium carbonate, potassium carbonate and the like, alkali hydrogen carbonate such as sodium hydrogen carbonate and the like, tertiary amines such as triethylamine, N,N-dimethylaniline, pyridine and the like, sodium hydride, sodium amide and the like may be used. The reaction can be carried out by stirring the reactants at 60° to 180° C. for 6 to 24 hours in an inert solvent. As the solvent, aprotic solvents such as N,N-dimethylformamide, N,N-dimethylacetamide, dimethysulfoxide, hexamethylphospholytriamide and the like, ethers such as dioxane, tetrahydrofuran and the like, aromatic hydrocarbons such as benzene, toluene, xylene and the like, or any mixture of those may be used.

It is preferable that the compound II, compound III-a or III-b and the base are mixed in a ratio of 1:1:1 to 3:1:5.

As to compounds which are included in the compounds II as one of starting materials and hard to obtain from the market, those can be synthesized in accordance with a method as disclosed in "J. Chem.Soc., C" page 2437 (1970), "Chem. Abstr." Vol. 81, 63569k (1974), "Chem. Abstr." Vol. 88.190714y (1978) or others. As to compound which are included in the compounds III-a or III-b and hard to obtain from the market, those can be synthesized in accordance with a method as disclosed in Japanese Unexamined Patent Application Gazette No. 156283/1981.

According to the invention, among the compounds shown by Formula (I), those represented by the formula

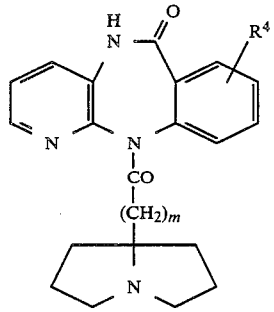

(I-b)

wherein $R^4$ and m have the meanings as referred to, can be prepared through one of following two routes A and B.

Route A

A process wherein a compound represented by the formula

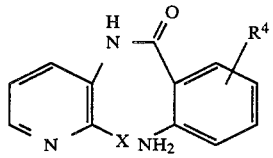

(IV)

wherein $R^4$ and X have the meanings as referred to, is reacted in the presence of a base with a compound represented by the formula

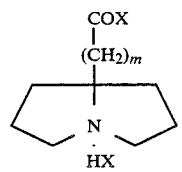

(V)

wherein X and m have the meanings as referred to, and the resulting compounds represented by the formula

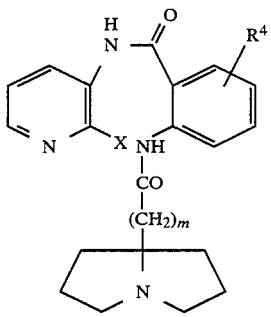

(VI)

wherein $R^4$, X and m have the meanings as referred to, is subjected to a ring closure treatment.

In this Route, alkali carbonates such as sodium carbonate, potassium carbonate and the like, alkali hydrogen carbonate such as sodium hydrogen carbonate and the like, tertiary amines such as triethylamine, N,N-dimethylaniline, pyridine and the like may be employed as the base. The reaction between the compounds IV and V can be carried out by stirring the reactants at −10° to 50° C. for 6 to 36 hours in an inert solvent. As the solvent, aprotic solvents such as N,N-dimethylformamide, N,N-dimethylacetamine, dimethylsulfoxide, hexamethylphospholytriamide and the like, ethers such as dioxane, tetrahydrofuran and the like, aromatic hydrocarbons such as benzene, toluene, xylene and the like, or any mixture of those may be used.

The ring closure treatment on the compound (VI) can be carried out by stirring same at 150° to 250° C. for 1 to 5 hours, in the presence or absence of a solvent. When the solvent is used for the treatment, it is preferable to select one having a higher boiling point, such as nitrobenzene, N,N-dimethylformamide, dimethylsulfoxide, decahydronaphthalene or the like, and a catalyst, for instance copper powder, cupric oxide or cuprous halogenides (cuprous chloride, cuprous bromide and cuprous iodide) may be employed to increase yield of the product.

Route B

A process wherein a compound represented by the formula

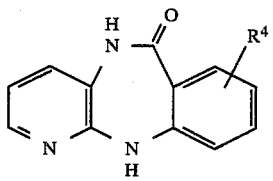

(VII)

wherein $R^4$ has the meaning as referred to, is reacted in the presence of a base with the copmpound shown by Formula V.

As the base, those referred to in the Route A can be employed. The reaction between the compounds VII and V can be carried out by stirring the reactants at 20° to 100° C. for 3 to 30 hours, in the presence of a solvent. As the solvent, aromatic hydrocarbons such as benzene, toluene, xylene and the like, or ethers such as diethyl ether, dioxane, tetrahydrofuran and the like may be used.

The compounds IV and VII as the starting materials for the Routes A and B can be synthesized according to a method as disclosed in U.S. Pat. No. 3,406,186, and the compounds V can be synthesized in accordance with a following route starting from a known compound which is represented by the formula

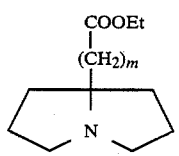

(III-b′)

wherein m has the meaning as referred to, and disclosed in Japanese Unexamined Patent Application Gazette No. 156283/1981.

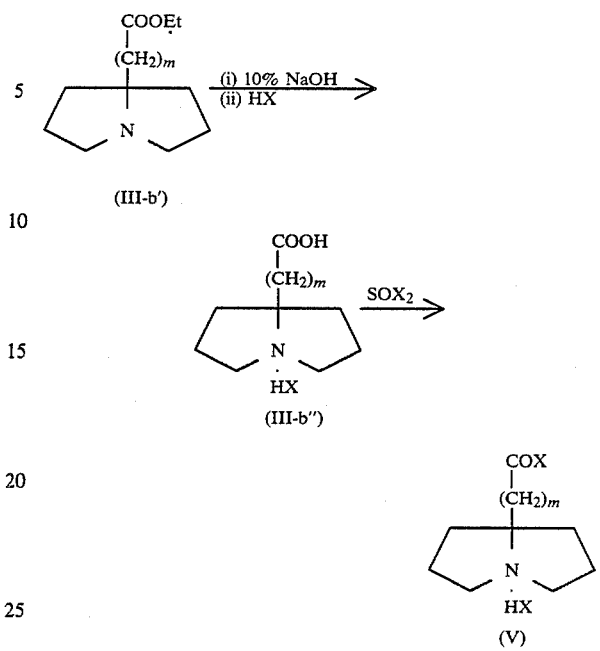

wherein X and m have the meanings as referred to.

When the compound or salt according to the invention is made into a pharmaceutical agent which contains the compound or salt as an effective one, there is no limitation in form therefor and thus it may be made into a solid agent such as a tablet, pill, capsule, powder, granule or suppository, or liquid agent such as a solution, suspension or emulsion, in a conventional manner.

In case of the solid agent, a starch, lactose, glucose, calcium phosphorate, magnesium stearate, gum arabic or the like vehicle can be used and if necessary, grossing agent, binder, breaking agent, coating agent, coloring agent or the like may also be used. The liquid agent may comprise a stabilizer, suspending agent, emulsifier, buffering agent, preserving agent or the like.

A dosing amount of the compound or salt for a patient is to be determined by taking a specific kind thereof, application form, symptoms and age of the patient as well as other various factors, but in general, it is preferable to give 0.1 to 2000 mg/day and more particularly 30 to 150mg/day for an adult.

PREFERRED EMBODIMENTS OF THE INVENTION

The invention will now be further explained with reference to Manufacturing Examples, Pharmacological Test Examples as well as Pharmaceutical Agent Preparing Examples.

EXAMPLE 1

10-(7a-Pyrrolizidinylmethyl)phenothiazine

A mixture of phenothiadine (13.0 g, 65.2 mmol) and sodium hydride (3.91 g. 97.8mmol, 60% dispersion in mineral oil) in 100 ml of anhydrous xylene was heated at 100° C. for 10 minutes. To the resulting reaction mixture, a solution of 7a-chloromethylpyrrolizidine hydrochloride (6.39 g. 32.6 mmol) in 100 ml of anhydrous N,N-dimethylformamide was added in dropwise and then further heated at reflux temperature for 12 hours. The solvent was evaporated in vacuo to give a solid which was subsequently partitioned between water and chloroform. The organic layer was washed with saturated sodium chloride solution, dried over anhydrous sodium sulfate, filtered and evaporated in vacuo to dryness. The remaining residue was chromatographed on silica gel, eluting with ethyl acetate/n-hexane/triethylamine (5:5:1) to give colorless crystals which were recrystallized from ethyl acetate to give 9.31g (88.6%) of the desired compound.

Melting point: 154°–156° C.

IR spectrum ($\nu_{max}^{kBr}$) cm$^{-1}$: 3050, 2950, 2850.

NMR spectrum (CDCl$_3$)$\delta$ppm : 0.90–2.20 (8H, m), 2.30–3.30 (4H, m), 4.00 (2H, s), 6.60–7.30 (8H, m).

Mass spectrum (EI/DI) m/z: 322 (M+), 110.

Elementary analysis: C$_{20}$H$_{22}$N$_2$S Cal.: C, 74.49; H, 6.88; N, 8.69. Found: C, 74.24; H, 7.19; N, 8.67.

EXAMPLE 2

10-[2-(7a-Pyrrolizidinyl)ethyl)phenothiazine

A mixture of phenothiadine (9.76 g, 49.0 mmol) and sodium hydride (2.94 g, 73.5 mmol, 60% dispersion in mineral oil) in 200 ml of anhydrous xylene was heated at 100° C. for 10 minutes. To the resulting reaction mixture, a solution of 7a-(2-chloroethyl)pyrrolizidine hydrochloride (5.15 g, 24.5 mmol) in 100 ml of anhydrous N,N-dimethylformamide was added in dropwise and then further heated at reflux temperature for 12 hours. The reaction mixture was treated as described in Example 1 to give 4.13 g (50.1%) of the desired compound.

Melting point: 91°–92° C.

IR spectrum ($\nu_{max}^{kBr}$) cm$^{-1}$: 3060, 2950, 2850, 2800.

NMR spectrum (CDCl$_3$)$\delta$ ppm: 1.40–2.20 (10H, m), 2.30–3.30 (4H, m), 3.95 (2H, t, J=7.0 Hz) 6.50–7.40 (8H, m).

Mass spectrum (EI/DI) m/z: 336 (M+), 110.

Elementary analysis: C$_{21}$H$_{24}$N$_2$S Cal.: C, 74.96; H, 7.19; N, 8.33. Found: C, 74.72; H, 7.24; N, 8.33.

EXAMPLE 3

2-(N,N-Dimethylsulfamoyl)-10-(7a-pyrrolizidinylmethyl)phenothiazine

A mixture of 2-(N,N-dimethylsulfamoyl)phenothiadine (12.2 g, 40.0 mmol) and sodium hydride (2.40 g, 60.0 mmol, 60% dispersion in mineral oil) in 240 ml of anhydrous xylene was heated at 150° C. for 10 minutes. To the resulting reaction mixture, a solution of 7a-chloromethylpyrrolizidine hydrochloride (3.92g, 20.0mmol) in 120ml of anhydrous N,N-dimethylformamide was added in dropwise and then further heated at reflux temperature for 2 hours. The resulting reaction mixture was treated as described in Example 1 to give 7.50 g (87.2%) of the desired compound.

Melting point: 101°–104° C.

IR spectrum ($\nu_{max}^{kBr}$)cm$^{-1}$: 2960, 2870, 1335, 1155.

NMR spectrum (CDCl$_3$)$\delta$ ppm: 1.30–2.10 (8H, m), 2.10–3.30 (4H, m), 2.68 (6H, s), 4.04 (2H, s), 6.80–7.70(7H, m).

Mass spectrum (EI/DI) m/z: 429(M+), 110.

Elementary analysis: C$_{22}$H$_{27}$N$_3$O$_2$S$_2$ Cal.: C, 61.51; H, 6.34; N, 9.78. Found: C, 61.21; H, 6.33; N, 9.51.

REFERENCE EXAMPLE 1

1-Trimethylsilylphenothiadine

Under an atmospher of argon, a solution of n-butyllithium in n-hexane (100 ml, 0.164 mol) was added in dropwise to a solution of 10-methoxymethylphenothiazine ["Chem. Abstr." 41:P2756f, 40.0 g, 0.164 mol) in 800 ml of tetrahydrofuran at 25° to 28° C. and the mixture was stirred for an hour at 35° to 40° C. To the reaction mixture, a solution of trimethylsilyl chloride (20.8 ml, 0.164 mol) was added and the reaction was further stirred for 2 hours at 35° to 40° C. The solvent was evaporated in vacuo to dryness and the remaining residue was partitioned between 800 ml of water and 1.2 liter of ethyl ether. The organic layer was dried over anhydrous sodium sulfate, filtered and evaporated in vacuo to dryness to give 51.8 g of crude product. The crude product was chromatographed on silica gel, eluting with n-hexane/ethyl acetate (50:1) to give 29.4 g (65.9%) of refined desired compound.

IR spectrum ($\nu_{max}^{KBr}$) cm$^{-1}$:3450, 3060, 2950, 1600, 1420, 1260.

NMR spectrum (CDCl$_3$)$\delta$ ppm: 0.43 (9H, s), 6.22 (1H, broad s), 6.50–7.40 (7H, m).

Mass spectrum (EI/DI) m/z:271 (M+), 255.

EXAMPLE 4

10-(7a-Pyrrolizidinylmethyl)-1-trimethylsilylphenothiazine

A mixture of 1-trimethylsilylphenothiazine (22.1 g, 81.4 mmol, prepared as described in Reference Example 1) and sodium hydride (7.16 g, 0.179 mol, 60% dispersion in mineral oil) in 300 ml of anhydrous xylene was heated at 100° C. for an hour. To the resulting reaction mixture, a solution of 7a-chloromethylpyrrolidine hydrochloride (16.0 g, 81.4 mmol) in 150 ml of anhydrous N,N-dimethylformamide was added in dropwise and then further heated at 100° C. for an hour. The solvent was evaporated in vacuo to dryness and the remaining residue was partitioned between water and dichloromethane. The organic layer was washed with saturated sodium chloride solution, dried over anhydrous sodium sulfate, filtered and evaporated in vacuo to dryness. The remaining residue was chromatographed on silica gel, eluting with n-hexane/ethyl acetate/triethylamine (50:1:1) to give colorless crystals which were recrystallized from n-hexane to give 11.4g (35.5%) of the desired compound.

Melting point: 150°–153° C.

IR spectrum ($\nu_{max}^{KBr}$) cm$^{-1}$:3060, 2950, 1585, 1405, 1260.

NMR spectrum (CDCl$_3$)$\delta$ ppm: 0.38(9H, s), 1.6–1.7 (8H, m), 2.2–3.2(4H, m), 3.93(2H, d, J=15.0 Hz), 6.8–7.6(7H, m).

Mass spectrum (EI/DI) m/z: 394(M+), 110.

Elementary analysis: C$_{23}$H$_{30}$N$_2$SSi Cal.: C, 70.00; H, 7.66; N, 7.10. Found: C, 69.71; H, 7.87; N, 7.02.

REFERENCE EXAMPLE 2

Pyrrolizidine-7a-carboxylic acid hydrochloride

A mixture of pyrrolizidine-7a-carboxylic acid ethylester (35.4 g, 0.193 mol) in 360 ml of 10% aqueous sodium hydroxide solution and 360 ml of ethanol was stirred at 10° to 15° C. for 2.5 hours. The reaction mixture was acidified with concentrated hydrochloric acid and then evaporated in vacuo to dryness. After addition of ethanol to the remaining residue, undissolved sodium chloride was filtered-off and the filtrate was evaporated in vacuo to dryness. The purifying operation described above was repeated twice. To the remaining residue, acetone was added to form crystals. The crystals were obtained through filtration and washed with small amount of acetone to give 34.2 g (92.4%) of the desired compound.

IR spectrum (94 $_{max}{}^{KBr}$) cm$^{-1}$:2800, 1720

NMR spectrum (DMSO-d$_6$)δ ppm : 1.40–2.60 (8H, m), 2.80–3.90 (4H, m).

Mass spectrum (EI/DI) m/z: 110.

REFERENCE EXAMPLE 3

Pyrrolizidine-7a-carbonyl chloride hydrochloride

A mixture of pyrrolizidine-7a-carboxylic acid hydrochloride (24.6 g, 0.128 mol, prepared as described in Reference Example 2) and thionylchloride (280 ml, 3.89 mol) was stirred for 17 hours at 20° to 25° C. and the excess of thionylchloride was evaporated in vacuo to give 25.7g (95.9%) of the desired compound, as yellowish solids.

IR spectrum ($\nu_{max}{}^{KBr}$) cm$^{-1}$:2960–2800, 1800, 1720.

REFERENCE EXAMPLE 4

2-Chloro-3-(2-(pyrrolizidine-7a-carbonyl)aminobenzoyl]aminopyridine

To a solution of 2-chloro-3-(2-aminobenzoyl)aminopyridine (15.0 g, 61.0 mmol), in 200 ml of anhydrous pyridine, pyrrolizidine-7a-carbonyl chloride hydrochloride (14.0 g, 80.5 mmol), prepared as described in Reference Example 3) was added at −20° C. The mixture was stirred for 17 hours at 10° C. and evaporated in vacuo to dryness. The remaining residue was partitioned between saturated sodium biscarbonate solution and chloroform. The organic layer was dried over anhydrous sodium sulfate, filtered and evaporated in vacuo to dryness. To the remaining residue, methanol was added. After stirring, the resulting crystals was obtained through filtration and washed with small amount of methanol to give 18.1 g (77.2%) of the desired compound.

Melting point: 199°–201° C.

IR spectrum ($\nu_{max}{}^{KBr}$) cm$^{-1}$:3225, 1600.

NMR spectrum (CDCl$_3$)δ ppm: 1.60–2.10 (6H, m), 2.10–2.90 (4H, m), 3.10–3.53 (2H, m), 7.00–7.80 (4H, m), 8.10–8.90 (4H, m), 12.0 (1H, broad s).

EXAMPLE 5

5,11-Dihydro-11-(pyrrolizidine-7a-carbonyl)-6H-pyrido(2,3-b)(1,4)-benzodiazepin-6-one and its dihydrochloride A mixture of 2-chloro-3-(2-(pyrrolizidine-7a-carbonyl)amino-benzoyl)aminopyridine (5.0 g, 13.0 mmol, prepared as described in Reference Example 4) and cuprous bromide (2.43 g, 17.0 mmol) was molten by heating same to 210° C. and stirred at same temperature for an hour. After cooling to room temperature, the reaction mixture was partitioned between 14% aqueous ammonia solution and chloroform. The organic layer was dried over anhydrous sodium sulfate, filtered and evaporated in vacuo to dryness. The remaining residue was chromatographed on silica gel, eluting with chloroform to give 2.7 g (59.0%) of the desired compound.

Melting point: 177°–178° C.

IR spectrum ($\nu_{max}{}^{KBr}$) cm$^{-1}$:1675, 1580.

NMR spectrum (CDCl$_3$)δ ppm: 1.60–2.13(6H, m), 2.16–3.00(4H, m), 3.20–3.56(2H, m), 7.00–7.63(3H, m), 7.86–9.00(4H, m), 13.03(1H, broad s).

Elementary analysis: C$_{20}$H$_{20}$N$_4$O$_2$ Cal.: C, 68.95; H, 5.79; N, 16.08. Found: C, 68.69; H, 5.73; N, 16.01.

50 ml of Ethyl ether solution saturated with hydrogen chloride (HCl: 0.12 mol) were added in dropwise to a solution of said free base (4.0 g, 11.5 mmol) in 80 ml of chloroform, under stirring in an ice bath. The resulting precipitate was obtained through filtration and washed with chloroform to give 3.81 g (72.7%) of the desired 5,11-dihydro-11-(pyrrolizidine-7a-carbonyl)-6H-pyrido[2,3-b](1,4)benzodiazepin-6-one dihydrochloride.

Melting point: 214° C. (dec.).

IR spectrum ($\nu_{max}{}^{KBr}$) cm$^{-1}$:1690, 1615.

NMR spectrum (CDCl$_3$)δ ppm: 2.00–2.56(6H, m), 2.56–2.90(4H, m), 3.40–4.00(2H, m), 7.16–8.56(7H, m).

PHARMACOLOGICAL TEST EXAMPLE 1

(Stress ulcer in rats)

Some pyrrolizidine compounds according to the invention were tested to evaluate their anti-ulcer activity in comparison with Pirenzepine and Cimetidine as controls, in accordance with the procedure proposed by Takagi et al.["Japan. J. Pharmacol." Vol. 18, page 9 (1968)].

Wistar rats of male sex were used, each having the body weight of 138 to 207 g. The animals were deprived of food for 24 hours prior to the test. They were immobilized in a restraint cage and immersed for 7 hours to the height of the xiphoid in a water bath kept at 23±1° C. After inflation with 10 ml of 1% formalin, the isolated stomach was opened along the greater curvature. The ulcer index was determined as the sum of the length (mm) of each erosion per rat. The compounds were administered orally an hour before the restraint.

Results are shown in following Table 1 in terms of percent inhibition of anti-ulcer activity with respect to concentrations of 10 to 100mg/kg. ED$_{50}$ represents the concentration of inhibitor which gives 50% inhibition.

From the results, it is obvious that the pyrrolizidine compounds according to the invention have intensive anti-ulcer activity on stress induced gastric ulcer.

TABLE 1

| Test compounds | Dose (mg/kg) | Number of animals | Inhibition (%) | ED$_{50}$ (mg/kg) |
| --- | --- | --- | --- | --- |
| Product of |  |  |  |  |
| Example 1 | 10 | 9 | 55.4 | <10 |
|  | 100 | 9 | 92.5 |  |
| Example 2 | 10 | 9 | 38.6 | 16.4 |
|  | 100 | 10 | 87.0 |  |
| Example 3 | 10 | 10 | 49.4 | 11.8 |
|  | 100 | 10 | 65.6 |  |
| Example 5 | 10 | 10 | 31.7 | 23.6 |
|  | 100 | 10 | 80.2 |  |
| Pirenzepine | 10 | 9 | 7.2 | 26.3 |
|  | 100 | 10 | 98.8 |  |
| Cimetidine | 10 | 9 | 16.9 | 33.8 |
|  | 100 | 10 | 81.5 |  |

PHRMACOLOGICAL TEST EXAMPLE 2

(Aspirin ulcer in rats)

Some pyrrolizidine compounds according to the invention were tested to evaluate their anti-ulcer activity on Aspirin ulcer, in comparison with Pirenzepine and Cimetidine as controls, in accordance with the procedure proposed by Okabe et al. ["Japan. J. Pharmacol." Vol. 24, page 363 (1974)].

Sprague-Dawley rats of male sex were used, each having the body weight of 146 to 210 g. The animals were deprived of food for 24 hours prior to the test. After an hour from oral administration of the compounds, the pylorus was ligated under anesthesia by ethyl ether and aspirin (100 mg/kg) suspended with 5% gum arabic was orally administered. After 7 hours from the administration, the stomach was isolated and inflated with 10 ml of 1% formalin. The ulcer index was determined as the sum of the length (mm) of each erosion per rat.

Results are shown in following Table 2 in terms of percent inhibition of anti-ulcer activity with respect to concentrations of 10 to 100 mg/kg. $ED_{50}$ represents the concentration of inhibitor which gives 50% inhibition.

From the results, it is obvious that the pyrrolizidine compounds according to the invention have intensive anti-ulcer activity on aspirin induced gastric ulcer.

TABLE 2

| Test compounds | Dose (mg/kg) | Number of animals | Inhibition (%) | $ED_{50}$ (mg/kg) |
| --- | --- | --- | --- | --- |
| Product of | | | | |
| Example 1 | 10 | 9 | 58.3 | <10 |
| | 100 | 9 | 63.5 | |
| Example 2 | 10 | 10 | 53.3 | <10 |
| | 100 | 10 | 73.2 | |
| Example 3 | 10 | 10 | 19.7 | >100 |
| | 100 | 9 | 36.5 | |
| Example 4 | 10 | 7 | 17.7 | 60.4 |
| | 100 | 8 | 65.6 | |
| Example 5 | 10 | 10 | 23.6 | 27.9 |
| | 100 | 10 | 82.2 | |
| Pirenzepine | 10 | 10 | 22.1 | 23.7 |
| | 100 | 10 | 90.5 | |
| Cimetidine | 10 | 9 | 12.2 | 50.4 |
| | 100 | 9 | 69.6 | |

PHARMACOLOGICAL TEST EXAMPLE 3

(Influence on pupil diameter of mice)

Some pyrrolizidine compounds according to the invention were tested to evaluate their influence on the pupil diameter of mice, in comparison with Pirenzepine and Atropine as controls.

ICR mice of male sex were used, each having the body weight of 16.3 to 20.5 g. The animals were deprived of food for 18 hours prior to the test. After 30 minutes from oral administration of the compounds, the pupil width was measured by a micrometer. Results are shown in following Table 3 in terms of ratio of pupil diameter and mydriatic effect.

The compounds according to the invention show a slight mydriatic effect which is to be caused by the inhibition of muscarinic receptor. And then, it is apparently shown that almost all compounds according to the invention are more weak in intensity of the mydriatic effect than that of Pirenzepine.

TABLE 3

| Test compounds | Dose (mg/kg) | Number of animals | Rate of pupil dia. (pre. = 1) | Ratio of mydriasis |
| --- | --- | --- | --- | --- |
| Product of | | | | |
| Example 1 | 30 | 3 | 2.7 | 0.57 |
| Example 2 | 30 | 3 | 4.6 | 0.98 |
| Example 3 | 30 | 3 | 1.1 | 0.23 |
| Example 5 | 30 | 3 | 0.9 | 0.19 |
| Pirenzepine | 30 | 3 | 3.4 | 0.72 |
| Atropine | 1 | 3 | 4.7 | 1.00 |

PHARMACOLOGICAL TEST EXAMPLE 4

(Acute toxicity in mice)

Some pyrrolizidine compounds according to the invention were tested to evaluate their acute toxicity in mice.

ICR mice of male sex were used, each having the body weight of 24.8 to 30.0 g. The compounds were orally administered and general condition, behavior and mortality were observed daily throughout the experimental period of time (7 days). At end of the period, the surviving animals were sacrificed. Dead animals were sacrificed at the time when they were recognized to be dead. $LD_{50}$ value was calculated in accordance with Litchfield-Wilcoxon's method.

Results are shown in following Table 4. It is clear that the toxicity of the compounds is low.

TABLE 4

| Test compound | Number of animals | $LD_{50}$ (mg/kg) |
| --- | --- | --- |
| Product of | | |
| Example 1 | 5 | >1000 |
| Example 2 | 5 | <1000 (4) |
| Example 3 | 5 | >1000 |
| Example 4 | 5 | >1000 |
| Example 5 | 5 | >1000 (1) |

Note: Numeral in the parenthesis represents the number of dead animals

PHARMACOLOGICAL AGENT PREPARATION EXAMPLE 1

(Tablet)

Following ingredients were mixed and treated in a conventional manner to obtain tablets.

| Product of Example 1 | 10.0 (mg) |
| --- | --- |
| Lactose | 148.0 |
| Corn starch | 60.0 |
| Magnesium stearate | 2.0 |
| | 220.0 mg/tablet |

PHARMACOLOGICAL AGENT PREPARATION EXAMPLE 2

(Capsule)

Following ingredients were mixed and treated in a conventional manner to obtain capsules.

| Product of Example 5 | 25.0 (mg) |
| --- | --- |
| Lactose | 144.0 |
| Corn starch | 30.0 |
| Magnesium stearate | 1.0 |
| | 200.0 mg/capsule |

PHARMACOLOGICAL AGENT PREPARATING EXAMPLE 3

(Granule)

Following ingredients were mixed and treated in a conventional manner to obtain granules.

| Product of Example 1 | 10.0 (mg) |
| --- | --- |
| Lactose | 260.0 |
| Corn starch | 220.0 |
| Hydroxypropyl cellulose | 10.0 |
| | 500.0 mg/wrapper |

PHARMACOLOGICAL AGENT PREPARATION EXAMPLE 4

(Injection)

An injection was prepared in a conventional manner with use of following ingredients and under sterile condition.

| | |
|---|---|
| Product of Example 5 (Dihydrochloride) | 2.0 (mg) |
| Sodium chloride | 8.0 |
| Distilled water | suitable amount |
| | 1.0 ml/vial |

What is claimed is:

1. A pyrrolizidine compound represented by the formula

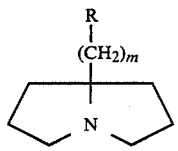
(I)

wherein
R is a radical of

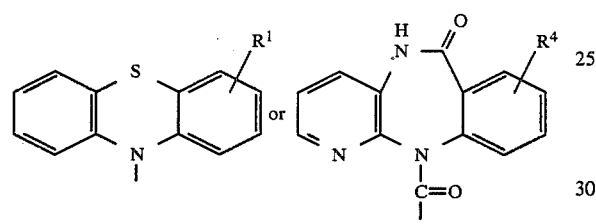

$R^1$ is hydrogen, halogen, alkyl group, alkoxy group, alkanoyl group, trifluoromethyl radical, trimethylsilyl radical or

$R^2$ and $R^3$ are same or different and are hydrogen or alkyl group, respectively, $R^4$ is hydrogen, halogen, alkyl group or alkoxy group and m is an integer of 0 to 5, and a salt thereof.

2. A compound and a salt thereof as claimed in claim 1, wherein said compound is 10-(7a pyrrolizidinylmethyl)phenothiazine.

3. A compound and a salt thereof as claimed in claim 1, wherein said compound is 10-[2-(7a-pyrrolizidinyl)ethyl]phenothiazine.

4. A compound and a salt thereof as claimed in claim 1, wherein said compound is 2-(N,N-dimethylsulfamoyl)-10-(7a-pyrrolizidinyl-methyl) phenothiazine.

5. A compound and a salt thereof as claimed in vlaim 1, wherein said compound is 10-(7a-pyrrolizidinylmethyl)-1-trimethylsilyl-phenothiazine.

6. A compound and a salt thereof as claimed in claim 1, wherein said compound is 5,11-dihydro-11-(pyrrolizidine-7a-carbonyl)-6H-pyrido-[2,3-b][1,4]benzodiazepin-6-one.

7. A process for the preparation of a pyrrolizidine compound represented by the formula

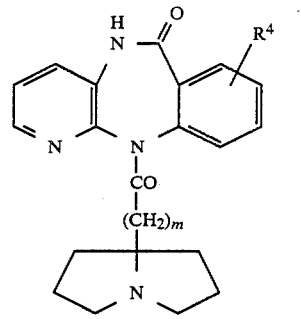
(I-b)

wherein
$R^4$ is hydrogen, halogen, alkyl group or alkoxy group and m is an integer of 0 to 5:
and a salt thereof, which comprises a step of reacting in the presence of a base a compound represented by the formula

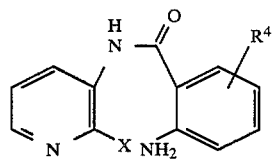
(IV)

wherein $R^4$ has the meaning as referred to and X is halogen, with a compound represented by the formula

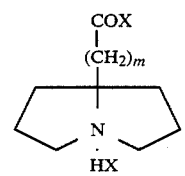
(V)

wherein X and m have the meanings as referred to, subjecting to a ring closing reaction the resulting compound represented by the formula

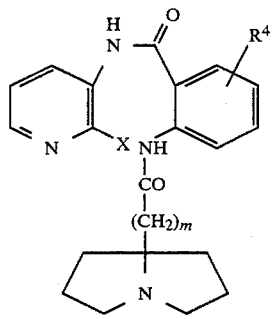
(VI)

wherein $R^4$, X and m have the meanings as referred to, and if necessary, converting the resulting ring-closed free base compound into the salt.

8. A pharmacological composition for the treatment of gastric ulcer, which comprises an anti-gastric ulcer effective amount of a pyrrolizidine compound of the formula

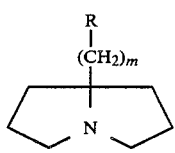 (I)

wherein
R is a radical of

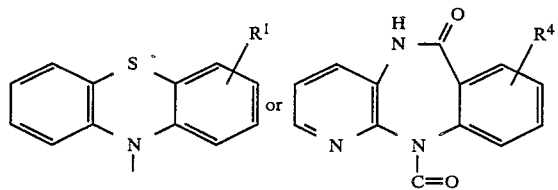

R¹ is hydrogen, halogen, alkyl group, alkoxy group, alkanoyl group, trifluoromethyl radical, trimethylsilyl radical or

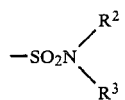

$R^2$ and $R^3$ are same or different and are hydrogen or alkyl group, respectively, $R^4$ is hydrogen, halogen, alkyl group or alkoxy group and m is an integer of 0 to 5, of a pharmaceutically acceptable salt thereof, and a pharmaceutically acceptable carrier.

9. A pharmaceutical composition as claimed in claim 8, wherein said pyrrolizidine compound is at least one of those selected from the group consisting of
  (a) 10-(7-pyrrolizidinylmethyl)phenothiazine,
  (b) 10-[2-(7a-pyrrolizidinyl)ethyl]phenothiazine,
  (c) 2-(N,N-dimethylsulfamoyl)-10-(7a-pyrrolizidinylmethyl)-phenbothiazine,
  (d) 10-(7a-pyrrolizidinylmethyl)-1-trimethylsilyphenothiazine,
  (e) 5,11-dihydro-11-(pyrrolizidine-7a-carbonyl)-6H-pyrido-[2,3-b]-[1,4]benzodiazepin-6-one, and
  (f) a pharmacologically acceptable salt of the compounds a to e.

* * * * *